(12) United States Patent
Nielsen et al.

(10) Patent No.: US 9,176,118 B2
(45) Date of Patent: Nov. 3, 2015

(54) METHODS EMPLOYING INSECT MODELS FOR DETERMINING INTESTINAL ABSORPTION OF CHEMICAL COMPOUNDS

(75) Inventors: Peter Aadal Nielsen, Oxie (SE); Gunnar Andersson, Roestaanga (SE); Olga Andersson, Roestaanga (SE)

(73) Assignee: Entomopharm ApS, Odense SV (DK)

( * ) Notice: Subject to any disclaimer, the term of this patent is extended or adjusted under 35 U.S.C. 154(b) by 211 days.

(21) Appl. No.: 13/387,083

(22) PCT Filed: Aug. 10, 2010

(86) PCT No.: PCT/EP2010/061590
§ 371 (c)(1),
(2), (4) Date: Jan. 25, 2012

(87) PCT Pub. No.: WO2011/018449
PCT Pub. Date: Feb. 17, 2011

(65) Prior Publication Data
US 2012/0122144 A1    May 17, 2012

Related U.S. Application Data

(60) Provisional application No. 61/233,151, filed on Aug. 12, 2009.

(51) Int. Cl.
*C12Q 1/00* (2006.01)
*G01N 33/50* (2006.01)

(52) U.S. Cl.
CPC .................................. *G01N 33/5085* (2013.01)

(58) Field of Classification Search
CPC ................................................ G01N 33/5085
See application file for complete search history.

(56) References Cited

U.S. PATENT DOCUMENTS 5,711,932 A     1/1998  Hirsh et al.
6,461,644 B1 *  10/2002 Jackson et al. ................ 424/499

OTHER PUBLICATIONS

Casartelli et al., 2005, J. Insect Physiology, vol. 51, pp. 933-940.*
Chamberlin M.E., 1998, J. Exp. Biol., vol. 141, pp. 295-311.*
Sviridov et al., 2006, Clinical Chemistry, vol. 53(3), pp. 389-397.*
Boudko et al. (2001, J. Experimental Biol., vol. 204, pp. 691-699).*
Wischke et al. (2006, Pharmazie, vol. 61, pp. 770-774).*
Maddrell et al. (1964, J. Exp. Biol., vol. 41, pp. 459-472).*
Scharrer et al. (1998, Cellular and Molecular Neurobiology, vol. 8(3), pp. 269-284).*
Casartelli et al., "Absorption of horseradish peroxidase in *Bombyx mori* larval midgut", *Journal of Insect Physiology*, vol. 53, 2007, pp. 517-525.
Fagerholm, "Prediction of human pharmacokinetics—gastrointestinal absorption", *Journal of Pharmacy and Pharmacology*, vol. 59, 2007, pp. 905-916.
Illa-Bochaca et al., "The regenerative nidi of the locust midgut as a model to study epithelial cell differentiation from stem cells", *The Journal of Experimental Biology*, vol. 209, 2006, pp. 2215-2223.
International Search Report and Written Opinion for International Application PCT/EP2010/061590 mailed Nov. 5, 2010.
Mortazavi et al., "Novel model for the in vivo study of central nervous system infection due to *Acanthamoeba* spp. (T4 genotype)", *Journal of Medical Microbiology*, vol. 58, 2009, pp. 503-508.
Shah et al., "Penetration of a Series of Dialkoxy Analogs of Dimethoate Through the Isolated Gut of Insects and Mammals", *Pesticide Biochemistry and Physiology*, vol. 2, 1972, pp. 324-330.

* cited by examiner

*Primary Examiner* — Anoop Singh
*Assistant Examiner* — David A Montanari
(74) *Attorney, Agent, or Firm* — Merchant & Gould P.C.

(57) ABSTRACT

There is provided insect screening models to determine gastrointestinal absorption of different chemical compounds in vertebrates, and in particular humans, in order to improve the compound screening procedures/processes in the early drug discovery process. This offers many advantages relative to prior technologies since insect models are more reliable tools for the decision-making process than the existing in vitro models, and will speed up the drug screening process and reduce the late phase attrition rate. Moreover, it will reduce the number of mammals sacrificed during the drug discovery phase.

5 Claims, No Drawings

METHODS EMPLOYING INSECT MODELS FOR DETERMINING INTESTINAL ABSORPTION OF CHEMICAL COMPOUNDS

This application is a National Stage Application of PCT/EP2010/061590, filed 10 Aug. 2010, which claims benefit of Ser. No. 61/233,151, filed 12 Aug. 2009 in the United States and which applications are incorporated herein by reference. To the extent appropriate, a claim of priority is made to each of the above disclosed applications.

FIELD OF THE INVENTION

The present invention relates to insect models that are aimed to reflect vertebrate absorption of chemical compounds, such as drugs, in the intestine or gut. Specifically, the models are based on a decapitated preparation of an insect, such as a locust, where a catheter is inserted into the midgut and hemolymph is sampled at various time points.

BACKGROUND OF THE INVENTION

Drug discovery is a costly affair where one of the major expenses in terms of money and time is the in vivo studies. In order to reduce these costs a large number of in vitro models are developed and applied as filters to select the most suitable compounds for the in vivo studies. However, in vitro models are often too simplified and may as such be misleading in the decision-making process. Hence, there is a demand for intermediate models that are more reliable than in vitro models and at the same time faster and cheaper than traditional vertebrate in vivo models.

The absorption of drugs via the oral route is a subject of intense and continuous investigation in the pharmaceutical industry since good bioavailability implies that the drug is able to reach the systemic circulation. Oral absorption is affected by both drug properties and the physiology of the gastrointestinal tract, including drug dissolution from the dosage form, the manner in which drug interacts with the aqueous environment and membrane, permeation across membrane, and irreversible removal by first-pass organs such as the intestine, liver, and lung (Martinez and Amidon, 2002).

The intestine, in addition to the liver, is an important tissue that regulates the extent of absorption of orally administered drugs, since the intestine and liver are involved in first-pass removal (Gibaldi et al., 1971; Rowland, 1972). The majority of drug absorption occurs at the small intestine where the presence of villi and microvilli markedly increases the absorptive area. The duodenum and jejunum possess the greatest surface areas due to the highest concentration of villi and microvilli in these regions, and surface area is least for the ileum (Magee and Dailey, 1986).

The intestine is unique in that the intestinal venous blood constitutes the majority of the blood supply to the liver, accounting for 75% of total liver blood flow. Drugs that are absorbed by the intestine, will reach the liver and the lung, for metabolism and for elimination (Gugler et al., 1975; Xu et al., 1989; Hirayama et al., 1990).

Since a large number of factors will affect the function of the intestine and thus also the uptake of orally administered drugs (Xu et al., 1989; Hirayama and Pang, 1990, Chen and Pang, 1997, Welling, 1984; Kimura and Higaki, 2002) there is a high demand on an intestinal model to be representative of the vertebrate intestinal function but also highly reproducible.

Because of the significance of the intestine as an important first pass organ after oral drug intake, high-throughput in vitro systems have been developed to assess intestinal absorption, metabolism, and excretion for the prediction of the bioavailability of a given chemical substance. Gene expression systems (Smit et al., 1998b; Cvetkovic et al., 1999; Gotoh et al., 2000; Shitara et al., 2002) provide direct information on the involvement of individual transporters or enzymes. Then there are the intestinal membrane segments/preparations (Wilson and Treanor, 1975; Hopfer et al., 1976; Lasker and Rickert, 1978; Johnson et al., 2001), cells (Koster and Noordhoek, 1983; Traber et al., 1991), everted sacs (Munck, 1965; Barr and Riegelman, 1970), and the Ussing chamber (Fiddian-Green and Silen, 1975). For flux measurements, a donor compartment is used for drug administration and a receiving compartment is used for sampling. With drug given to the mucosal side, sampling allows the examination of drug absorption, metabolism, and efflux as well as entry into the basolateral compartment. Moreover, a drug may be given at the serosal compartment to ascertain the net flux from the basolateral side to the mucosal lumen.

A popular in vitro system is the Caco-2 cell line, derived from human colon carcinoma cells (Hidalgo et al., 1989). A drawback is the existence of a unstirred water layer that may pose as a barrier for lipophilic drug transport (Hidalgo et al., 1991). The development of the Caco-2 penetration model has greatly facilitated progress and led to the testing of diverse drug classes as Pgp substrates (Burton et al., 1993).

The in situ vascularly perfused rat small intestine preparation is a useful preparation for studying the disposition of both orally and systemically administered agents (Windmueller and Spaeth, 1977, and Doherty and Pang, 2000). In this preparation, the native architecture of the small intestine is maintained with respect to the circulation such that the extents of metabolism, absorption, and secretion can be studied simultaneously. The technique allows for single-pass or recirculating experiments involving systemic or luminal drug administration, including luminal administration in closed loops or segments.

In vivo techniques exist for the study of intestinal drug absorption. The Doluisio method entails use of an in situ rat gut technique for drug administration into the lumen (Doluisio et al., 1969). In some rat preparations, the inflow and outflow of a select segment were monitored for drug disappearance, and arterial blood was sampled and the volume of blood was replenished by transfusion (Barr and Riegelman, 1970). Some studies involve luminal instillation of drug to selected or closed segments of rats (duodenum, jejunum, or ileum) (Hirayama et al., 1990) or humans (Gramatté and Richter, 1994).

The alimentary tract of insects is divided into three main regions: the foregut, midgut and the hindgut. Both the foregut and the hindgut are of ectodermal origin while the midgut is of endodermal origin. The cells in the foregut are usually flattened and are not involved in absorption or secretion. Part of the foregut is a crop which is a storage organ and in most insects an extensible part of the foregut. The effectiveness of the crop as a storage organ (especially for fluid feeding insects) is underlined by its impermeability to hydrophilic molecules. In orthopteroid insects the crop is developed into a grinding apparatus with strong cuticular plates or teeth which brake up the food.

The cells of the midgut are actively involved in enzyme production as well as in absorption of nutrients. The majority of cells are so called principal cells. These cells are tall columnar cells and similar to the enterocytes in the vertebrate intestine, these cells exhibit huge numbers of microvilli towards the luminal side. This morphology strongly indicates that the principle cells are very metabolically active and are main players in nutrient absorption and secretion of digestive enzymes (Lehane and Billingsley, 1996). Also similar to vertebrate intestine there are proliferative zones or nidi in the midgut, with the same function as stem cells in vertebrate intestine (Illa-Bochaca and Montuenga, 2006). Since the principal cells in the insect midgut, similar to vertebrate enterocytes, have a limited life span there is a need for a high regenerative capacity. The undifferentiated cells, daughter cells from the nidi, give rise to both differentiated columnar principal cells and endocrine cells.

The hindgut is usually differentiated into pylorus, ileum and rectum. The main function of this part of the intestine is to absorb water that has been delivered into the Malpighian tubule and therefore the cells in this part of the intestine are metabolically active.

Since plant feeding insects also have to handle compounds contained in the food that may be toxic to the insect an efficient cytochrome P-450 system has been developed, which will convert these compounds into water soluble products and excreted via the Malpighian tubule. The P-450 system is highly represented in the midgut.

The structure and function of the insect intestine makes it a strong candidate for studying intestinal drug uptake and could be a relevant model for highly efficient studies and early characterization, documentation and selection of compounds intended for oral administration.

It is an object of the present invention to use insect models that are aimed to reflect vertebrate absorption of drugs in the intestine or gut.

SUMMARY OF THE INVENTION

The overall object of the present invention is to develop insect screening models to determine gastrointestinal absorption of different chemical compounds in order to improve the compound screening procedures/processes in the early drug discovery phase. This object offers many advantages relative to prior technologies since insect models are more reliable tools for the decision-making process than the existing in vitro models, and will speed up the drug screening process and reduce the late phase attrition rate. Moreover, it will reduce the number of mammals sacrificed during the drug discovery phase.

The present inventors have surprisingly found that the midgut in insects has more in common with the intestine of mammals than previously assumed. It has been found that the midgut in these insects is actively involved in enzyme production as well as in absorption of nutrients in a way very similar to that observed in humans.

Accordingly, the present invention relates to insect models that are aimed to reflect vertebrate absorption of chemical compounds, such as drugs, in the intestine or gut. Specifically, the models are based on a decapitated preparation of an insect, such as a locust, where a catheter is inserted into the midgut and hemolymph is collected, e.g. by insertion of another catheter into the abdomen, by calibrated microcapillary tubes, by a syringe, by pipette or other means. The model permits the study of drug uptake from the relevant part of the intestine into the hemolymph. Compared to oral administration in a rodent, the present model permits the rapid testing as an early stage assessment of the ability of the compound to pass the intestinal mucosa and be selected as candidates for oral administration. Another advantage is the fact that the actual amount of compound exposed to the intestine is well controlled using a decapitated preparation of an insect.

The insects of the present invention may therefore serve as an intermediate model for determination of gastrointestinal absorption of chemical compounds.

The present invention is thus able to provide for the first time rational strategies for generating a simple in vivo system for determining a compound's absorption in the intestine.

In one aspect, the invention provides a method for predicting intestinal absorption of a chemical compound, such as a drug, in vertebrates, said method comprises the steps of:
  decapitating an insect;
  inserting a first catheter or a probe into the midgut of the insect;
  collecting hemolymph e.g. by insertion of a second catheter into the abdomen of the insect or by using calibrated microcapillary tubes, a Hamilton syringe or a pipette
  administering the chemical compound to the midgut of the insect through the first catheter;
  taking one or more hemolymph samples;
  determining the concentration of the drug in the one or more hemolymph samples; and
  calculating the absorption of the drug.

In a preferred embodiment of the present invention the insect is selected from the group consisting of the orders Dictyoptera, Orthoptera, Hymenoptera, Diptera, Cheleutoptera, and Lepidoptera. In order to ensure efficient absorption in the midgut the chemical compound is preferably administered to the midgut of the insect through a catheter or a probe.

In addition the present invention provides a model insect for determining intestinal absorption of a chemical compound, such as a drug, in vertebrates, said model obtained by a method comprising the steps:
  decapitating an insect;
  inserting a first catheter or a probe into the midgut of the insect; and
  collecting hemolymph e.g. by insertion of a second catheter into the abdomen of the insect or by using calibrated microcapillary tubes, a Hamilton syringe or a pipette
  administering the chemical compound to the midgut of the insect through the first catheter;
  taking one or more hemolymph samples;
  determining the concentration of the drug in the one or more hemolymph samples; and
  calculating the absorption of the drug.

Preferably the insect is selected from the group consisting of the orders Blattoidea, Acridoidea, Cheleutoptera, Apine, Brachycera, and Lepidoptera.

In a particularly preferred embodiment of the present invention the insects are selected from the Acridoidea (locusts) and Blattodea (cockroaches) orders.

In various aspects and embodiments the present invention provides the subject-matter set out in the claims below.

DETAILED DESCRIPTION OF THE INVENTION

The present invention provides a new methodology for initial assessment and prediction of intestinal uptake of various chemical compounds. The invention is generally particular useful for efficient screening of newly synthesized compounds in the early phase of drug discovery.

A drug in accordance with the present invention is defined in its broadest scope as a chemical compound that, when absorbed into the body of a living organism, alters normal bodily function. More specifically, a drug in accordance with the present invention is a chemical compound that may be used in the treatment, cure, prevention, or diagnosis of disease or used to otherwise to enhance physical or mental well-being. Of particular interest in accordance with the present invention are psychoactive drugs, which are chemical compounds that cross the BBB and acts primarily upon the central nervous system where it alters brain function, resulting in changes in perception, mood, consciousness, cognition and behavior.

The present invention relates to but is not restricted to the use of insects selected from the following orders (Taxonomy according to: Djurens Värld, Ed B. Hanström; Förlagshuset Norden A B, Malmö, 1964):

| Order | Suborder/family | Comment |
|---|---|---|
| Dictyoptera | Blattoidea | Cockroach |
| | Mantoidea | |
| Orthoptera | Grylloidea | Crickets |
| | Acridoidea | Grasshoppers |
| Cheleutoptera | | Stick insects |
| Lepidoptera | | Moths |
| Hymenoptera | Formicoidea | Ants |
| | Vespoidea | Wasps |
| | Apoidea | Bee like Hymenopterans |
| | Bombinae | Bumble-bees |
| | Apine | Proper bees |
| Odonata | | Dragonflies |
| Diptera | Nematocera | Mosquitos |
| | Brachycera | Flies E.g *Drosophila* |

The invention will also relate to the following orders comprising insect species relevant for the intestinal uptake assessment method:

| Order | Suborder/family | Comment |
|---|---|---|
| Ephemerida | | Mayflies |
| Plecoptera | | |
| Dermoptera | Forficuloidea | Earwigs |
| Homoptera | Cicadinea | Cicadas |
| | Aphidine | Plant-louse |
| Heteroptera | | Hemipteran |
| Coleoptera | | Beetles |
| Trichoptera | | Caddis fly |

The present invention preferably uses large insects, such as the migratory locust, Locusta migratoria and the desert locust, Schistocera gregaria or cockroach where it's feasible to administer test compounds and subsequently take hemolymph for analyses of the concentration of the absorbed compound. The locust has been used to develop the model since it's a large insect and has an alimentary tract and a midgut that is very well characterised.

Accordingly, the present invention focuses on insect models that are aimed to reflect the vertebrate intestinal uptake of the test compounds. Investigations of the intestinal uptake profile are of extreme importance in compound selection during the early phase of drug discovery.

In accordance with a preferred embodiment of present invention the migratory locust, Locusta migratoria and/or the desert locust, Schistocera gregaria, is used since it is easy to breed and it is a relatively large insect with relevant size of the midgut and hemolymph volumes relevant for quantitative measurement of concentrations of compounds taken up.

EXAMPLES

In a preferred embodiment of present invention the insects are selected from the order Acridoidea and specifically Locusta migratoria and Schistocera gregaria are used. The insects may be obtained from local suppliers or bred in house. The grasshoppers were reared under crowded conditions at 28° C. and a 12:12 dark:light photocycle and fed fresh grass and bran. Before experiments the grasshoppers were fed ecologically cultivated wheat for two weeks. Animals used are adult males (in some experiments females) between two to four weeks after adult emergence. After decapitation, test compounds are administrated via a catheter or a probe inserted into the midgut of the animal. At various times after administration hemolymph samples are taken for quantitative determination of drug concentration in the hemolymph. The samples are snap-frozen and stored until analyses. Drug concentration is analysed by HPLC, LC/MSMS or other methods.

In the following the present invention is exemplified in further detail.

Example 1

The head of male locusts (Locusta migratoria), which have been starving for 12 hours, was cut off and a plastic catheter was inserted under microscope into the esophagus. 20 µl of aminomodified fluorescent polystyrene nano particles (100 nm) was administered via the catheter by using a Hamilton syringe.

10 and 30 minutes after administration hemolymph samples were collected with a calibrated (10 µl) capillary tube by puncturing the ventral membrane anterior to the thorax. The hemolymph samples were analyzed by fluorescence microscopy and no fluorescent nano particles were detectable in the hemolymph samples.

Example 1 shows that the insect intestine is a functional barrier, which prevents large polystyrene nano particles administered orally to enter the hemolymph. This reflects the functionality of the vertebrate intestinal barrier which also prevents diffusion of orally administered large molecules into the blood.

Example 2

The head of male locusts (Locusta migratoria), which have been starving for 12 hours, was cut off and a plastic catheter was inserted under microscope into the esophagus. 20 µl of quinidine (0.1 mg/ml) was administered via the catheter by using a Hamilton syringe.

10 and 30 minutes after administration (10 µl) hemolymph was collected with a calibrated capillary tube by puncturing the ventral membrane anterior to the thorax and immediately blown into a tube containing 40 µl aqua dest and 100 µl of acetonitrile. Each sample was centrifuged for 5 minutes (10 000g at 4° C.). 100 µl of the supernatants were transferred to new test tubes for LCMS analysis. The analysis did not show any detectable quantity of quinidine at 10 or 30 minutes.

Example 3

The head of male locusts (Locusta migratoria), which have been starving for 12 hours, was cut off and a plastic catheter was inserted under microscope into the esophagus. 20 µl of quinidine (1 mg/ml) was administered via the catheter by using a Hamilton syringe. 10 and 30 minutes after administration (10 µl) hemolymph was collected with a calibrated capillary tube by puncturing the ventral membrane anterior to the thorax and immediately blown into a tube containing 40 µl aqua dest and 100 µl of acetonitrile. Each sample was centrifuged for 5 minutes (10 000g at 4° C.). 100 µl of the supernatants were transferred to new test tubes for LCMS analysis.

The average quinidine concentrations measured in the hemolymph after 10 and 30 minutes were 2960 ng/ml and 1465 ng/ml respectively.

Example 4

The head of male locusts (Locusta migratoria), which have been starving for 12 hours, was cut off and a plastic catheter was inserted under microscope into the esophagus. 20 µl of propranolol (0.1 mg/ml) was administered via the catheter by using a Hamilton syringe.

10 and 30 minutes after administration (10 µl) hemolymph was collected with a calibrated capillary tube by puncturing the ventral membrane anterior to the thorax and immediately blown into a tube containing 40 µl aqua dest and 100 µl of acetonitrile. Each sample was centrifuged for 5 minutes (10 000g at 4° C.). 100 µl of the supernatants were transferred to new test tubes for LCMS analysis. The average propranolol concentrations measured in the hemolymph after 10 and 30 minutes were 102 ng/ml and 61 ng/ml respectively.

Example 5

The head of male locusts (Locusta migratoria), which have been starving for 12 hours, was cut off and a plastic catheter was inserted under microscope into the esophagus. 20 µl of propranolol (1 mg/ml) was administered via the catheter by using a Hamilton syringe.

10 and 30 minutes after administration (10 µl) hemolymph was collected with a calibrated capillary tube by puncturing the ventral membrane anterior to the thorax and immediately blown into a tube containing 40 µl aqua dest and 100 µl of acetonitrile. Each sample was centrifuged for 5 minutes (10 000g at 4° C.). 100 µl of the supernatants were transferred to new test tubes for LCMS analysis. The average propranolol concentrations measured in the hemolymph after 10 and 30 minutes were 1081 ng/ml and 1564 ng/ml respectively.

Example 6

The head of male locusts (Locusta migratoria), which have been starving for 12 hours, was cut off and a plastic catheter was inserted under microscope into the esophagus. 20 µl of caffeine (0.1 mg/ml) was administered via the catheter by using a Hamilton syringe. 10 and 30 minutes after administration (10 µl) hemolymph was collected with a calibrated capillary tube by puncturing the ventral membrane anterior to the thorax and immediately blown into a tube containing 40 µl aqua dest and 100 µl of acetonitrile. Each sample was centrifuged for 5 minutes (10 000g at 4° C.). 100 µl of the supernatants were transferred to new test tubes for LCMS analysis. The average caffeine concentrations measured in the hemolymph after 10 and 30 minutes were 177 ng/ml and 276 ng/ml respectively.

Example 7

The head of male locusts (Locusta migratoria), which have been starving for 12 hours, was cut off and a plastic catheter was inserted under microscope into the esophagus. 20 µl of caffeine (1 mg/ml) was administered via the catheter by using a Hamilton syringe. 10 and 30 minutes after administration (10 µl) hemolymph was collected with a calibrated capillary tube by puncturing the ventral membrane anterior to the thorax and immediately blown into a tube containing 40 µl aqua dest and 100 µl of acetonitrile. Each sample was centrifuged for 5 minutes (10 000g at 4° C.). 100 µl of the supernatants were transferred to new test tubes for LCMS analysis. The average caffeine concentrations measured in the hemolymph after 10 and 30 minutes were 1154 ng/ml and 1655 ng/ml respectively.

Example 8

The head of male locusts (Locusta migratoria), which have been starving for 12 hours, was cut off and a plastic catheter was inserted under microscope into the esophagus. 20 µl of atenolol (0.1 mg/ml) was administered via the catheter by using a Hamilton syringe. 10 and 30 minutes after administration (10 µl) hemolymph was collected with a calibrated capillary tube by puncturing the ventral membrane anterior to the thorax and immediately blown into a tube containing 40 µl aqua dest and 100 µl of acetonitrile. Each sample was centrifuged for 5 minutes (10 000g at 4° C.). 100 µl of the supernatants were transferred to new test tubes for LCMS analysis. The average atenolol concentrations measured in the hemolymph after 10 and 30 minutes were 458 ng/ml and 318 ng/ml respectively.

Example 9

The head of male locusts (Locusta migratoria), which have been starving for 12 hours, was cut off and a plastic catheter was inserted under microscope into the esophagus. 20 µl of atenolol (1 mg/ml) was administered via the catheter by using a Hamilton syringe. 10 and 30 minutes after administration (10 µl) hemolymph was collected with a calibrated capillary tube by puncturing the ventral membrane anterior to the thorax and immediately blown into a tube containing 40 µl aqua dest and 100 µl of acetonitrile. Each sample was centrifuged for 5 minutes (10 000g at 4° C.). 100 µl of the supernatants were transferred to new test tubes for LCMS analysis. The average atenolol concentrations measured in the hemolymph after 10 and 30 minutes were 336 ng/ml and 121 ng/ml respectively.

Example 2-9 include the compounds: Quinidine, a Pgp substrate that can be expected to be poorly taken up at low doses due to an efflux mechanism; Caffeine, a compound of high permeability that is transcellularly taken up by passive diffusion; Propranolol and Atenolol, two beta blockers with markedly different ADME properties. From the examples 2-9 it is seen that at low (0.1 mg/ml) concentration there was no detectable uptake of quinidine in the hemolymph. However, after caffeine administration the average hemolymph concentration was 177 ng/ml and 276 ng/ml after 10 and 30 minutes respectively. The average hemolymph concentration after 10 minutes of the two beta blockers propranolol and atenolol were 177 ng/ml and 458 ng/ml, respectively. At the high (1.0 mg/ml) concentration the average hemolymph concentration of quinidine was 2960 ng/ml after 10 minutes. Also after 10 minutes the average caffeine concentration was 1154 ng/ml and for the two beta blockers, propranolol and atenolol the average concentrations were 1080 ng/ml and 336 ng/ml, respectively.

Thus, as expected there was a marked uptake of caffeine following low dose administration. Also as expected there was no detectable uptake of the Pgp substrate compound quinidine at the low concentration. However, at the high dose where the efflux transporter is saturated there is a high permeability for quinidine in agreement with the FDA classification of this drug. The hemolymph concentration at the low dose (0.1 mg/ml) was lower for the high permeability beta blocker propranolol compared to the low permeability blocker atenolol. However, human studies have shown that the longer half life and smaller volume of distribution results also in human in higher plasma atenolol concentrations compared to propranolol (Carmona et al. 2009). Thus the present data obtained in the locust model highly correlate to data obtained in humans. At the high dose (1.0 mg/ml), there was a dose related increase in caffeine and propranolol hemolymph concentrations. However, there was no increase in atenolol uptake. This may be explained by the fact that atenolol is a class 3 compound according to the Biopharmaceutics Classification System and for these compounds uptake transporters are the major determinants of drug availability (Shugarts and Benet, 2009).

References

Martinez MN and Amidon GL (2002) A mechanistic approach to understanding the factors affecting drug absorption: a review of fundamentals. *J Clin Pharmacol* 42: 620-643

Gibaldi M, Boyes RN, and Feldman S (1971) The influence of first pass effect on availability of drugs. *J Pharm Sci* 60: 1338-1340

Rowland M (1972) The influence of route of administration on drug availability. *J Pharm Sci* 101: 70-74

Magee DF and Dailey AF II (1986) *Digestion and The Structure and Function of The Gut* (*Karger Continuing Education Series*, vol. 8). Karger, Basel.

Gugler R, Lain P, and Azarnoff DL (1975) Effect of portacaval shunt on the disposition of drugs with and without first-pass effect. *J Pharmacol Exp Ther* 195: 416-423

Xu X, Hirayama H, and Pang KS (1989) First pass metabolism of salicylamide Studies in the once through vascularly perfused rat intestine-liver preparation *Drug Metab Dispos* 17: 556-563

Hirayama H, Morgado J, Gasinska I, and Pang KS (1990) Estimations of intestinal and liver extraction in the in vivo rat: studies on gentisamide conjugation. *Drug Metab Dispos* 18: 580-587

Hirayama H and Pang KS (1990) First-pass metabolism of gentisamide: influence of intestinal metabolism on hepatic formation of conjugates. Studies in the once-through vascularly perfused rat intestine-liver preparation. *Drug Metab Dispos* 18: 580-587

Chen J and Pang KS (1997) Effect of flow on first-pass metabolism of drugs: single pass studies on 4-methylumbelliferone (4MU) conjugation in the serially perfused rat intestine and liver preparations. *J Pharmacol Exp Ther* 280: 24-31

Welling PG (1984) Effects of gastrointestinal disease on drug absorption, in *Pharmadynamic Basis for Drug Treatment* (Benet LZ, Massoud N, and Gambertoglio JG eds) pp 29-47, Raven Press, New York Kimura T and Higaki K (2002) Gastrointestinal transit and drug absorption. *Biol Pharm Bull* 25: 149-164

Smit JW, Weert B, Schinkel AH, and Meijer DK (1998b) Heterologous expression of various P-glycoproteins in polarized epithelial cells induces directional transport of small (type 1) and bulk (type 2) cationic drugs. *J Pharmacol Exp Ther* 286: 321-327

Cvetkovic M, Leake B, Fromm MF, Wilkinson GR, and Kim RB (1999) OATP and P-glycoprotein transporters mediate the cellular uptake and excretion of fexofenadine. *Drug Metab Dispos* 27: 866-871

Gotoh Y, Suzuki H, Kinoshita S, Hirohashi T, Kato Y, and Sugiyama Y (2000) Involvement of an organic anion transporter (canalicular multispecific organic anion transporter/multidrug resistance-associated protein 2) in gastrointestinal secretion of glutathione conjugates in rats. *J Pharmacol Exp Ther* 292: 433-439

Shitara Y, Sugiyama D, Kusuhara H, Kato Y, Abe T, Meier PJ, Itoh T, and Sugiyama Y (2002) Comparative inhibitory effects of different compounds on rat oatp1 (slc21a1)- and Oatp2 (Slc21a5)-mediated transport. *Pharm Res (NY)* 19: 147-153

Wilson FA and Treanor LL (1975) Characterization of the passive and active transport mechanisms for bile acid uptake into rat isolated intestinal epithelial cells. *Biochim Biophys Acta* 406: 280-293

Hopfer U, Sigrist-Nelson K, and Groseclose R (1976) Jejunal and ileal D-glucose transport in isolated brush border membranes. *Biochim Biophys Acta* 426: 349-353

Lasker J and Rickert DE (1978) Absorption and glucuronosylation of diethylstilbestrol by the rat small intestine. *Xenobiotica* 8: 665-672

Johnson BM, Charman WN, and Porter C JH (2001) The impact of P-glycoprotein efflux on enterocyte residence time and enterocyte-based metabolism of verapamil. *J Pharm Pharmacol* 53: 1611-1619

Koster AS and Noordhoek J (1983) Glucuronidation in isolated perfused rat intestinal segments after mucosal and serosal administration of 1-naphthol. *J Pharmacol Exp Ther* 226: 533-538

Traber PG, Gumucio DL, and Wang W (1991) Isolation of intestinal epithelial cells for the study of differential gene expression along the crypt-villus axis. *Am J Physiol* 260: G895-G903

Munck BG (1965) Amino acid transport by the small intestine of the rat. The effect of amino acid pre-loading on the trans-intestinal amino acid transport by the everted sac preparation. *Biochim Biophys Acta* 109: 142-150

Barr WH and Riegelman S (1970) Intestinal drug absorption and metabolism. I. Comparison of methods and models to study physiological factors of in vitro and in vivo intestinal absorption. *J Pharm Sci* 59: 154-163

Fiddian-Green RG and Silen W (1975) Mechanisms of disposal of acid and alkali in rabbit duodenum. *Am J Physiol* 229: 1641-1648

Hidalgo IJ, Raub TJ, and Borchardt RT (1989) Characterization of the human colon carcinoma cell line (Caco-2) as a model system for intestinal epithelial permeability. *Gastroenterology* 96: 736-749

Hidalgo IJ, Hillgren KM, Grass GM, and Borchardt RT (1991) Characterization of the unstirred water layer in Caco-2 cell monolayers using a novel diffusion apparatus. *Pharm Res (NY)* 8: 222-227

Burton PS, Conradi RA, Hilgers AR, and Ho NF (1993) Evidence for a polarized efflux system for peptides in the apical membrane of Caco-2 cells. *Biochem Biophys Res Commun* 190: 760-766

Windmueller HG and Spaeth AE (1977) Vascular perfusion of rat small intestine: metabolic studies with isolated and in situ preparations. *Fed Proc* 36: 177-181

Doherty M and Pang KS (2000) Route-dependent metabolism of morphine in the vascularly perfused rat small intestine preparation. *Pharm Res (NY)* 17: 290-297

Doluisio JT, Billups NF, Dittert LW, Sugita ET, and Swintosky JV (1969) Drug Absorption. I. An in situ rat gut technique yielding realistic absorption rates. *J Pharm Sci* 58: 1196-1200

Hirayama H, Morgado J, Gasinska I, and Pang KS (1990) Estimations of intestinal and liver extraction in the in vivo rat: studies on gentisamide conjugation. *Drug Metab Dispos* 18: 580-587

Gramatté T and Richter K (1994) Paracetamol absorption from different sites in the human small intestine. *Br J Clin Pharmacol* 37: 608-611

Illa-Bocgaca I and Montuenga L M (2006) The regenerative nidi of the locust as a model to study epithelial cell differentiation from stem cells. *J Exp Biol* 209: 2215-2223.

Lehane M J and Billingsley P R (1996) Biology of the insect midgut. London: Chapman and Hall

The invention claimed is:

1. A method for assessing intestinal absorption of a drug in an insect, said method comprises the steps of:
   (i) decapitating an insect;
   (ii) inserting a first catheter or a probe into the midgut of the insect, wherein the midgut is not removed from the insect and remain intact within the insect;
   (iii) collecting hemolymph from the intack midgut;
   (iv) administering the drug to the intact midgut of the insect through the first catheter;
   (v) taking one or more hemolymph samples from the intact midgut;
   (vi) determining the concentration of the drug in the one or more hemolymph samples; and
   (vii) calculating the absorption of the drug.

2. The method of claim 1, wherein the insect is selected from the group consisting of the orders Dictyoptera, Orthoptera, Hymenoptera, Diptera, Cheleutoptera, and Lepidoptera.

3. The method of claim 1, wherein the concentration of the drug is determined by liquid chromotomagraphy/mass spectrometry (LC/MS).

4. The method according to claim 1, wherein step (iii) is performed by insertion of a second catheter, calibrated microcapillary tubes, a Hamilton syringe or a pipette into the abdomen of the insect.

5. The method according to claim 1, wherein the drug is a psychoactive drug.

* * * * *